United States Patent [19]

Kötzsch et al.

[11] Patent Number: 4,609,749

[45] Date of Patent: Sep. 2, 1986

[54] METHOD FOR THE SIMULTANEOUS PREPARATION OF CARBOXYLIC ACID TRIMETHYLSILYL ESTERS AND SILYLATED CARBOXYLIC ACID AMIDES

[75] Inventors: Hans-Joachim Kötzsch, Rheinfelden; Hans-Joachim Vahlensieck, Wehr, both of Fed. Rep. of Germany

[73] Assignee: Dynamit Nobel AG, Cologne, Fed. Rep. of Germany

[21] Appl. No.: 800,979

[22] Filed: Nov. 22, 1985

[30] Foreign Application Priority Data

Dec. 1, 1984 [DE] Fed. Rep. of Germany ....... 3443961

[51] Int. Cl.$^4$ ................................................. C07F 7/10
[52] U.S. Cl. .................................................... 556/411
[58] Field of Search ........................................ 556/411

[56] References Cited

U.S. PATENT DOCUMENTS 3,839,387 10/1974 Chow et al. ......................... 556/411
4,059,559 11/1977 Burkhardt et al. .................. 556/411

*Primary Examiner*—Paul F. Shaver
*Attorney, Agent, or Firm*—Felfe & Lynch

[57] ABSTRACT

Carboxylic acid trimethylsilyl esters (I) and trimethylsilyl carboxylic acid amides can be prepared simultaneously from the corresponding carboxylic acid anhydrides; the esters (I) and monocarboxylic acid trimethylsilyl amides are formed first and can then be recovered, or else the bis-trimethylsilyl carboxylic acid amides are formed by further transposition with trimethylchlorosilane in the presence of tertiary amines, and are separated from the carboxylic acid trimethylsilyl ester (I) and recovered.

10 Claims, No Drawings

METHOD FOR THE SIMULTANEOUS PREPARATION OF CARBOXYLIC ACID TRIMETHYLSILYL ESTERS AND SILYLATED CARBOXYLIC ACID AMIDES

BACKGROUND OF THE INVENTION

The invention relates to a method for the simultaneous preparation of carboxylic acid trimethylsilyl esters of the formula R-COOSi(CH$_3$)$_3$ (I) and of carboxylic acid trimethylsilyl amides of the formula RCONHSi(CH$_3$)$_3$ (IV) or N.N- and N.O-bis-trimethylsilylcarboxylic acid amides of formulas II and III, respectively:

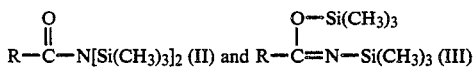 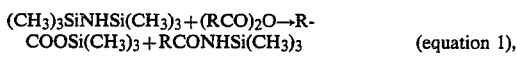

The N.O isomers of formula III are preferred. II and III were not separated. R represents preferably CH$_3$, C$_2$H$_5$, C$_3$H$_7$, CH(CH$_3$)$_2$, CH$_2$=CH, CH$_2$=CCH$_3$, CH$_2$F, CHF$_2$ or CF$_3$, but R generally can originate from carboxylic acid anhydrides of the formula (RCO)$_2$O (V) which can be reacted with hexamethyldisilazane.

According to the state of the art, the acylation of hexamethyldisilazane to form substances of formula I (R=CH$_3$) has already been attempted with ketene (Chem. Abstr. 57, 11224c), but it is difficult to control. The yield is impaired by undesired byproducts which prevent obtaining a pure and stable product.

With carboxylic acid chlorides, in the presence in some cases of an acid acceptor, the acylation is performed with an unsatisfactory yield and with the formation of many byproducts, especially with degradation to nitrile compounds.

The preparation of carboxylic acid trimethylsilyl amides RCONHSi(CH$_3$)$_3$ (IV) has been performed heretofore from acid amides RCONH$_2$ with hexamethyldisilazane (G. Schirawski and U. Wannagat, Monatshefte Chem. 1969, 100 (6), 1901–9). The special disadvantage in this case is the occurrence of byproduct having a triazine structure. Furthermore, unusable ammonia is undesirably released.

The conventional methods for the preparation of persilylated carboxylic acid amides of formulas II and III from carboxylic acid amides with trimethylchlorosilane and a tertiary amine as acid acceptor (L. Birkhofer and A. Ritter, Angew. Chem. 75, 93–4, 1963) causes the formation of very large amounts of salts of two equivalents of tertiary amine hydrochloride. Resorting to high dilution requires large amounts of solvents that have to be processed, limits the capacity, and leads to delayed reaction. In the case of incomplete transformation, contaminated products of poor shelf life are obtained.

Accordingly, the problem presents itself of finding an improved, simple method for the preparation not only of carboxylic acid trimethylsilyl esters but also of silylated carboxylic acid amides.

THE INVENTION

The subject matter of the invention is a method for the simultaneous production of carboxylic acid trimethylsilyl esters and trimethylsilyl carboxylic acid amides by reacting a carboxylic acid anhydride at 40° to 130° C., preferably at 50° to 90° C., with hexamethyldisilazane to form carboxylic acid trimethylsilyl esters and mono-trimethylsilylcarboxylic acid amides and, if desired, after further reaction with one mole of trimethylchlorosilane for each mol of mono-trimethylsilyl carboxylic acid amide at 40° to 80° C., in the presence of one mole of tertiary amine, separating tertiary amine hydrochloride as a solid substance from the mixture of the products, and separating the bis-silyl derivatives by further processing.

The process of preparation runs according to the following reaction equations:

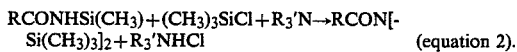 (equation 1), as well as:

$$RCONHSi(CH_3) + (CH_3)_3SiCl + R_3'N \rightarrow RCON[Si(CH_3)_3]_2 + R_3'NHCl \quad \text{(equation 2).}$$

Surprisingly, both reactions take place very completely, virtually without the formation of byproducts.

According to the invention, first a transposition of hexamethylsilazane with the carboxylic acid anhydride takes place with the splitting off of the disilazane according to equation 1, which, if a molar ratio of 1:1 is used, or an excess of hexamethyldisilazane, yields carboxylic acid trimethylsilyl ester (I) and the monosilylated carboxylic acid amide (IV) as the only isolatable products. This product mixture of I and IV can be worked up, by distillation for example, and yields the two products I and IV in pure, merchantable form.

To prepare the bis-trimethylsilyl carboxylic acid amides, the product mixture according to equation 1 can be further reacted, in accordance with equation 2, with one mole of trimethylchlorosilane with the addition of one mole of tertiary amine as acid acceptor. After the tertiary amine hydrochloride has been separated as a solid substance, products I and II and/or III are then obtained in pure form by distillation. The carboxylic acid trimethylsilyl esters (I) are not attacked in the reaction according to equation 2 with trimethylchlorosilane and they remain unaltered.

Accordingly, the monosilylated carboxylic acid amide IV obtained according to equation 1 by working up the product can be reacted with trimethylchlorosilane and tertiary amine; also, additional mono-trimethylsilyl carboxylic acid amide, preferably of the same kind, can be added to a reaction mixture according to equation 1, while the reaction is to be performed according to equation 2 with molar amounts of trimethylchlorosilane and tertiary amine according to the amount of mono-trimethylsilylcarboxylic acid amide (IV) then present.

In the work-up by distillation, the esters I, and the persilylated amides II or III, are obtained pure or in mixtures of both forms and, if desired, the monosilylated amide IV is obtained in very pure form, separately from one another.

This method makes it possible for the first time to obtain carboxylic acid trimethylsilyl esters (I) simply and in a high yield, which formerly were accessibly only with difficulty and in low yields.

The process requires no solvents and, in comparison with known methods, it can be performed with a higher product concentration and by a complete and rapid reaction.

It is a special advantage that, when the reactions according to equations 1 and 2 are performed successively, only half of the tertiary amine hydrochloride that occurs as solid salt in conventional methods and has to be separated and worked up again, is produced by performing the reactions according to equations 1 and 2 successively. If the reaction according to equation 1 is performed alone, no solid substance is produced that has to be processed.

The reaction according to equation 1, and the fact that it can be performed simply, completely and smoothly, is not suggested in the state of the art in connection with the transposition with ketene or acid chlorides; instead, a complex reaction and the formation of considerable amounts of byproducts, such as undesirable nitrile compounds and hexamethyl disiloxane, was to be expected.

The molar ratios of the reactants are generally to correspond precisely to the information given in the reaction equations 1 and 2. An excess of one reactant is possible, but leads to contamination or to residues that must be separated. An excess of hexamethyldisilazane above the molar ratio of 1:1 according to equation 1, and amounting to as much as 8 moles, is possible and desirable, for example if the use of a diluent is desirable.

The method is practiced in a simple manner by placing hexamethyldisilazane, in an excess if desired, in a reactor, at 40° to 80° C., and dosing in no more than one equivalent of carboxylic acid anhydride, with stirring. The reaction is relatively mildly exothermic. A temperature of 130° C. is not to be exceeded. Cooling is to be performed if necessary.

After the reaction has ended, the mixture can be processed in a known manner to yield the carboxylic acid trimethylsilyl esters I and the mono-carboxylic acid trimethylsilyl amides IV, in a manner known in itself. Both products give very high yields and contain no byproducts due to the manner in which the process is performed. It is possible to separate only the esters I by distillation and to react the distillation residue or the isolated compound IV according to reaction equation 2.

In accordance with the invention, it is possible without product separation to perform the further silylation according to reaction equation 2 by the admixture of one equivalent of trimethylchlorosilane for each equivalent of monotrimethylsilyl carboxylic acid amide IV. After the establishment of the reaction temperature of 40° to 80° C., one equivalent of tertiary amine is dosed in without exceeding the maximum temperature of 80° C., and the reaction is thus carried out.

After the reaction, the tertiary amine hydrochloride, which is in solid form, is separated by a filtering device, such as a centrifuge for example, and the mixture of the silylation products is delivered to a vacuum distillation column and fractionally distilled.

The filter cake is washed, preferably with the carboxylic acid trimethyl silyl ester in question, and transferred to a solid-matter stirrer, such as an anchor stirrer, or paddle dryer equipped with a vacuum distillation apparatus, dried by low-vacuum distillation, and saturated with ammonia. Preferably this is done with the exclusion of water. The tertiary amine that is released is distilled out and reused. At the same time the ammonium chloride, which does not appreciably sublimate at 40° to 80°, is dried.

A stirrer reactor with reflux condenser and dosing apparatus, which is equipped for the exclusion of moisture and for temperature control, serves as the apparatus for the practice of the method of the invention.

The reaction products can be separated into their components in a distillation apparatus equipped for vacuum distillation. The mono-silylamides (IV) can also be precipitated by crystallization at low temperature and separated by filtration or centrifugation.

It is, however, preferred to proceed with the reaction of the reaction mixture according to reaction equation 1, without such separation, or to perform the further reaction with trimethylchlorosilane after distilling out the carboxylic acid esters I. The reaction according to reaction equation 2 is performed, for example, in the stirrer reactor described above. The addition of trimethylchlorosilane is performed at the reaction temperature or lower. By the addition of the tertiary amine, preferably by dosing as the reaction progresses, the reaction is started and performed at temperatures from 40° to 80° C. In some cases a postreaction period is necessary.

The tertiary amine hydrochloride is separated from the reaction mixture by filtration or centrifugation. The silylation products are worked up in the above-described distillation apparatus equipped for vacuum distillation.

Carboxylic acid anhydrides of the formula $(RCO)_2O$ (V) suitable for use as starting substances will depend on the kind of radical R that is required in the product, especially in carboxylic acid ester I. Preferred, for example, are acetic anhydride, the anhydrides of propionic, butyric and isobutyric acid, acrylic and methacrylic acid anhydride, and the anhydrides of mono-, di- and trifluoroacetic acid.

Suitable acid acceptors are tertiary amines, preferably trimethylamine, triethylamine, tributylamine, N.N-dimethylaniline and pyridine.

Preferred products of Formulas II or of Formulas III or IV are, for example:
N-trimethylsilylacetamide
N-trimethylsilylpropionamide
N-trimethylsilylbutyramide
N-trimethylsilylisobutyramide
N-trimethylsilylmethacrylamide
N-trimethylsilyltrifluoracetamide
bis-trimethylsilylacetamide
bis-trimethylsilylpropionamide
bis-trimethylsilylisobutyramide
bis-trimethylsilylacrylamide bis-trimethylsilylmethacrylamide
bis-trimethylsilylfluoracetamide
bis-trimethylsilyltrifluoracetamide,
which serve as silylation and protective-group reagents. They find application in the synthesis of antibiotics and natural substances, and in the treatment of solid-bed catalysts.

Examples of preferred products of formula I which are formed simultaneously are trimethyl silylacetate, acrylate, methacrylate, fluoroacetate and trifluoroacetate. Products of formula I find application especially in the inertiation of silanols by controlled terminal group locking with the trimethylsilyl group, and likewise as silylating agents.

EXAMPLES

Example 1: Preparation of trimethylsilyl acetate and N-trimethylsilyl acetamide In a 1.4 cubic-meter still, equipped with a stirrer, an 800-liter dosing apparatus, thermostat heater and a vacuum distillation apparatus (Sulzer fine-vacuum packing with 30 trays), a top condenser, distillate lines, and controlledtemperature receiver, 4 kmol (644 kg) of hexamethyldisilazane was heated to 72° C. Over a period of two hours, 4 kmol (408 kg) of acetic acid anhydride was stirred in, the internal temperature rising momentarily to 93° C. Then stirring was continued for three hours at about 80° C. and, after transformation was complete, the mixture was fractionally distilled in vacuo.

The distillation yielded a total of 514 kg (97% yield) of pure trimethylsilyl acetate, b.p. 39° C. (approx. 50 mbar), and thereafter (with the temperature in the top condenser, distillate line and receiver controlled at 37° C.) 501 kg (95.6% yield) of N-trimethylsilyl acetamide, b.p. 59° C. (1 mbar), m.p. 35° C.

Example 2: Preparation of trimethylsilyl acetate and N,N- or N.O-bis-trimethylsilyl acetamide In a 2 cubic-meter stirrer reactor with thermostat-controlled heating and cooling circuit in the jacket, a nitrogen-flooded reflux condenser and a submerged gas introduction tube, 4.1 kmol (660 kg) of hexamethyldisilazane was heated to 72° C. Over a period of two hours, 4 kmol (408 kg) acetic acid anhydride was stirred in, the internal temperature rising momentarily to 91° C. Then stirring was continued for four hours at approximately 80° C. Then the material was cooled to approximately 52° C. 4 kmol (434 kg) of trimethylchlorosilane was mixed in, and, over a period of about one hour, a total of 238 kg (4 kmol) of trimethylamine was added, with stirring, through a flow meter at the rate of about 4 kg/min, while the reactor temperature was raised again to 72° C. by means of the heating circuit. After the end of the amine addition, the mixture was stirred for four more hours at about 72° C. to complete the reaction.

For the separation of the products, the fully reacted raw product suspension was pumped from the reactor through an automatically operating siphon centrifuge into the solid trimethylammonium chloride (approx. 420 kg; washing liquid trimethylsilyl acetate) and separated into the raw filtrate.

The raw filtrate consisted of about 60 wt.-% of N.N- or N.O-bis-trimethylsilyl acetamide, about 30 wt.-% of trimethylsilyl acetate and about 1 wt.-% of hexamethyl disilazane. The vacuum distillation through the distillation apparatus described in Example 1 yielded a total of 512 kg of trimethylsilyl acetate (97% yield), b.p. 40° C. (50 mbar) and 799 kg of N.N- or N.O-bis-trimethylsilyl acetamide (97% yield), b.p. 44° C. (11 mbar), with a hexamethyldisilazane content of about 0.8%.

The centrifugally separated trimethylammonium chloride was transferred directly from the centrifuge to a paddle dryer, placed under vacuum, and the vacuum was relieved with approximately 80 kg of gaseous ammonia. Under its own pressure, the mixture was heated to about 80° C. and finally the pressure was relieved by cautiously opening the vapor line, whereupon the trimethylamine that had been released was distilled into a low-temperature receiver, (yielding approximately 230 kg) and prepared for reuse. After changing receivers, and while maintaining the 80° C. dryer temperature, the apparatus was evacuated to about 50 mbar, whereupon another 30 kg, approximately, of trimethyl silyl acetate distilled out. Then 210 kg of usable ammonium chloride was removed from the dryer in the form of a white powder.

Example 3: Preparation of trimethylsilyltrifluoroacetate and N.N- or N.O-bis-trimethylsilyltrifluoroacetate In a ten-liter stirrer reactor having a thermostat-controlled heating and cooling water circuit in the jacket, a nitrogen-blanketed reflux condenser, an internal thermometer and a one-liter dosing apparatus with introduction tube, 1,620 g (10 mol) of hexamethyldisilazane was heated at 60° C. Over a period of two hours, 2,100 g (10 mol) of trifluoroacetic acid anhydride was stirred in, raising the internal temperature momentarily to 84° C. Then stirring was continued for three hours at about 80° C. Then the mixture was cooled to about 56° C. 1,085 g (10 mol) of trimethylchlorosilane was stirred in, and 790 g (10 mol) of pyridine was added drop by drop with stirring, while the reactor temperature was raised by means of the heating circuit to 74° C. After the addition of amine was ended, the mixture was stirred for another three hours at about 74° C. to complete the reaction.

After the separation of the pyridine hydrochloride (approx. 1,200 g) with a centrifuge with the exclusion of moisture, the filtrate was fractionated in vacuo through a Sulzer column.

The distillation yielded a total of 1,722 g (92.6% yield) of trimethylsilyltrifluoroacetate, b.p. 43° C. (approx. 100 mbar) and 2,408 (93.7% yield) of N.N- and N.O-bis-trimethylsilyl trifluoroacetamide, b.p. 40° C. (25 mbar).

The 1,200 g of pyridine hydrochloride was treated with about 200 g of liquid ammonia in the cold, in a glass autoclave with anchor stirrer. The exothermic reaction ended in about 20 minutes. Then the pyridine was distilled off with stirring, at 80° C. and about 50 mbar, ultimately at 20 mbar after replacing the receiver. Thus a total of 719 g (92% yield) of pyridine was recovered.

Example 4: Preparation of trimethylsilyl methacrylate and N.N- or N.O-bis-trimethylsilyl methacrylamide In a manner similar to Example 3, 1,610 g (10 mol) of hexamethyldisilazane together with 1,580 g of methacrylic acid trimethylsilyl ester (stabilized with 500 mg of copper powder) were placed in the reactor and heated to 66° C. Over a period of two hours, 1,540 g (10 mol) of freshly distilled methacrylic acid anhydride was stirred in, raising the internal temperature momentarily to 79° C. Then stirring was continued for four hours at 79° C. After cooling to about 56° C., 1,085 g (10 mol) of trimethylchlorosilane was mixed in and 1,010 g (10 mol) of triethylamine was added drop by drop, with stirring, over a period of one hour, while the reactor temperature was raised to 72° C. by means of the heating circuit. By centrifugation about 1.4 kg of triethylamine hydrochloride was separated and the filtrate was fractionated in a Sulzer column with monel packing while feeding in pure oxygen in traces for stabilization.

The distillation yielded a total of 3,092 g of methacrylic acid trimethylsilyl ester (95.7% yield, after subtracting the amount added as additional diluent), b.p. 40° C. (11 mbar, and 2,110 g of N.N- or N.O-bis-trimethylsilyl methacrylamide (92% yield), b.p. 36° C. (1 mbar).

The triethylamine hydrochloride was worked up similarly to Example 3, and a total of 944 g (94%) of triethylamine was recovered by distillation at about 80 mbar, and ultimately, after changing receivers, at about 40 mbar.

It will be understood that the specification and examples are illustrative but not limitative of the present invention and that other embodiments within the spirit and scope of the invention will suggest themselves to those skilled in the art.

We claim:

1. A method for the simultaneous preparation of carboxylic acid trimethylsilyl esters and trimethylsilyl carboxylic acid amides, comprising reacting a carboxylic acid anhydride of the formula $(RCO)_2O$ at 40° to 130° C., preferably at 50°–90° C., with hexamethyldisilazane to form carboxylic acid trimethylsilyl esters and monotrimethylsilyl carboxylic acid amides.

2. The method of claim 1 further comprising additionally reacting one mole of trimethylchlorosilane for each mole of mono-trimethylsilyl carboxylic acid amide at 40° to 80° C. in the presence of one mole of tertiary amine for each mole of the acid amide, separating tertiary amine x HCl and working up the silyl derivatives.

3. The method according to claim 2, wherein the carboxylic acid trimethylsilyl ester is recovered after the reaction with hexamethyldisilazane and monotrimethylsilylcarboxylic acid amide is separated.

4. The method according to claim 3, wherein the monotrimethylsilyl carboxylic acid amide is reacted only with trimethylchlorosilane in the presence of tertiary amine.

5. The method according to claim 2, wherein the amine is released with ammonia from the separated tert.-amine x HCl and obtained by distillation.

6. The method according to claim 3, wherein the amine is released with ammonia from the separated tert.-amine x HCl and obtained by distillation.

7. The method according to claim 4, wherein the amine is released with ammonia from the separated tert.-amine x HCl and obtained by distillation.

8. The method according to claim 1, wherein R represents preferably $CH_3$, $C_2H_5$, $C_3H_7$, $CH(CH_3)_2$, $CH_2=CH$, $CH_2=CCH_3$, $CH_2F$, $CHF_2$, or $CF_3$.

9. The method according to claim 2, wherein R represents preferably $CH_3$, $C_2H_5$, $C_3H_7$, $CH(CH_3)_2$, $CH_2=CH$, $CH_2=CCH_3$, $CH_2F$, $CHF_2$, or $CF_3$.

10. The method of claim 9, wherein the tertiary amine is trimethylamine, triethylamine, tributylamine, N.N-dimethylaniline and pyridine.

* * * * *